(12) United States Patent
Sahin et al.

(10) Patent No.: US 10,151,748 B2
(45) Date of Patent: Dec. 11, 2018

(54) DEVICES AND METHODS FOR DETERMINING MOLECULAR STRUCTURE

(71) Applicant: THE TRUSTEES OF COLUMBIA UNIVERSITY IN THE CITY OF NEW YORK, New York, NY (US)

(72) Inventors: Ozgur Sahin, New York, NY (US); Duckhoe Kim, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 15/130,251

(22) Filed: Apr. 15, 2016

(65) Prior Publication Data

US 2016/0223528 A1 Aug. 4, 2016

Related U.S. Application Data

(63) Continuation of application No. PCT/US2014/061230, filed on Oct. 17, 2014.

(60) Provisional application No. 61/892,274, filed on Oct. 17, 2013.

(51) Int. Cl.
*G01N 33/53* (2006.01)
*C12Q 1/68* (2018.01)

(52) U.S. Cl.
CPC ......... *G01N 33/5308* (2013.01); *C12Q 1/68* (2013.01)

(58) Field of Classification Search
None
See application file for complete search history.

(56) References Cited

U.S. PATENT DOCUMENTS

| 8,067,169 B2 | 11/2011 | Sahin |
| 2010/0175155 A1 | 7/2010 | Sahin |

FOREIGN PATENT DOCUMENTS

| WO | WO 2008/073378 A2 | 6/2008 |
| WO | WO 2009/117517 A2 | 9/2009 |

OTHER PUBLICATIONS

Sahin. "Angstrom-Scale Multicolor Chemical Force Microscopy". Jun. 18, 2013. Flyer for Seminar held by the Laboratory of Physics of Living Matter. (Year: 2013).*
Dong et al., "A Nanomechanical Interface to Rapid Single-Molecule Interactions", Nature Communications 2(247):1-6 (2011).
Hopf et al., "Three-Dimensional Structures of Membrane Proteins from Genomic Sequencing", Cell 149:1607-1621 (2012).
International Search Report dated Feb. 20, 2015 in International Application No. PCT/US14/61230.
Kim et al., "Angstrom-Scale Chemical Microscopy: Multicolor Single-Molecule Imaging With Energy Landscape Engineering", Biophysical Journal 104(2): Supplement 1, p. 381a (2013).

(Continued)

*Primary Examiner* — Joseph G. Dauner
(74) *Attorney, Agent, or Firm* — Baker Botts L.L.P.

(57) ABSTRACT

A method of determining the structure of a molecule can include labeling a first location on the molecule with a first DNA strand, and measuring a force-time waveform using the twisting of a T-shaped atomic force microscope cantilever scanning across the molecule. The cantilever can include a DNA probe having a first region that is complimentary to the first DNA strand.

6 Claims, 11 Drawing Sheets

Specification includes a Sequence Listing.

(56) References Cited

OTHER PUBLICATIONS

Merkel et al., "Energy landscapes of receptor-ligand bonds explored with dynamic force spectroscopy", Nature 397:50-53 (1999).
Nanoword Ultrashort Cantilevers [online]. NanoWorld. 2011 [retrieved on Feb. 2, 2015]. Retrieved from the Internet: <URL: http://www.highspeedscanning.com/ultra-short-cantilevers>; pp. 1-5.
Sahin, "Harnessing Bifurcations in Tapping-Mode Atomic Force Microscopy to Calibrate Time-Varying Tip-Sample Force Measurements", Review of Scientific Instruments 78:103707-1 to 103707-4 (2007).
Voulgarakis et al., "Sequencing DNA by Dynamic Force Spectroscopy: Limitations and Prospects", Nano Letters 6(7):1483-1486 (2006).

\* cited by examiner

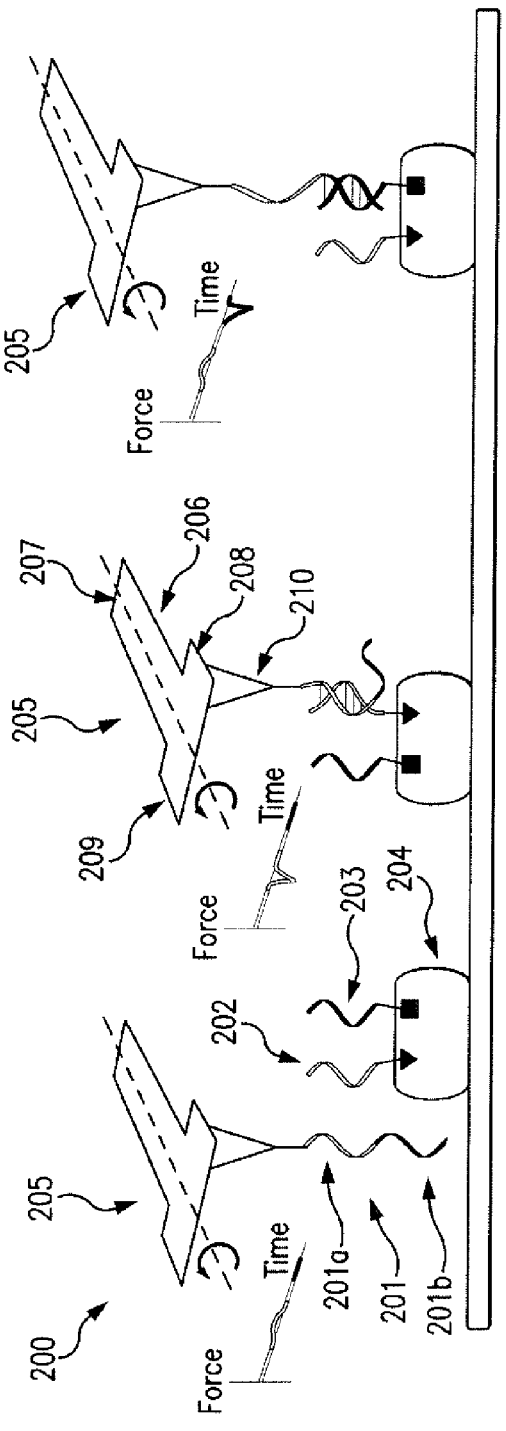
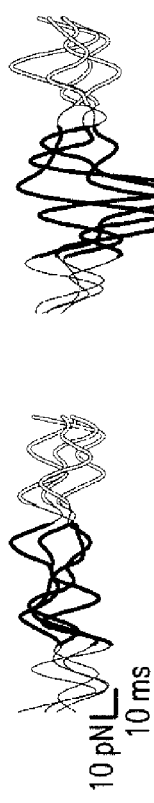
FIG. 3A  FIG. 3B  FIG. 3C
FIG. 3D  FIG. 3E  FIG. 3F

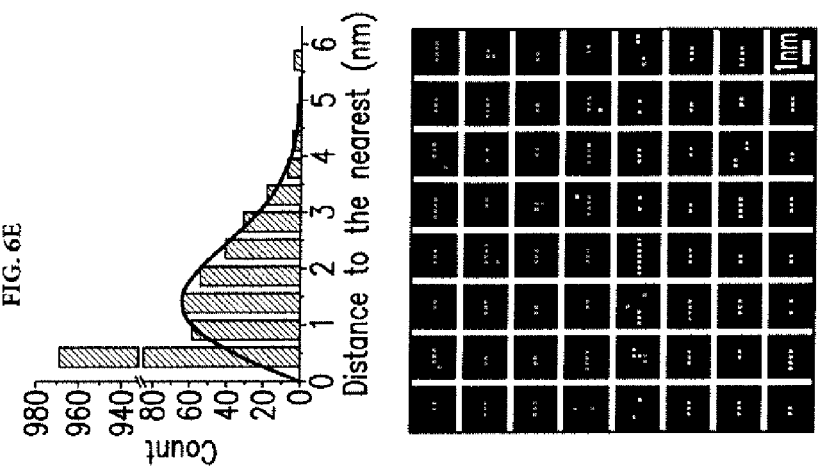
FIG. 6E
FIG. 6F
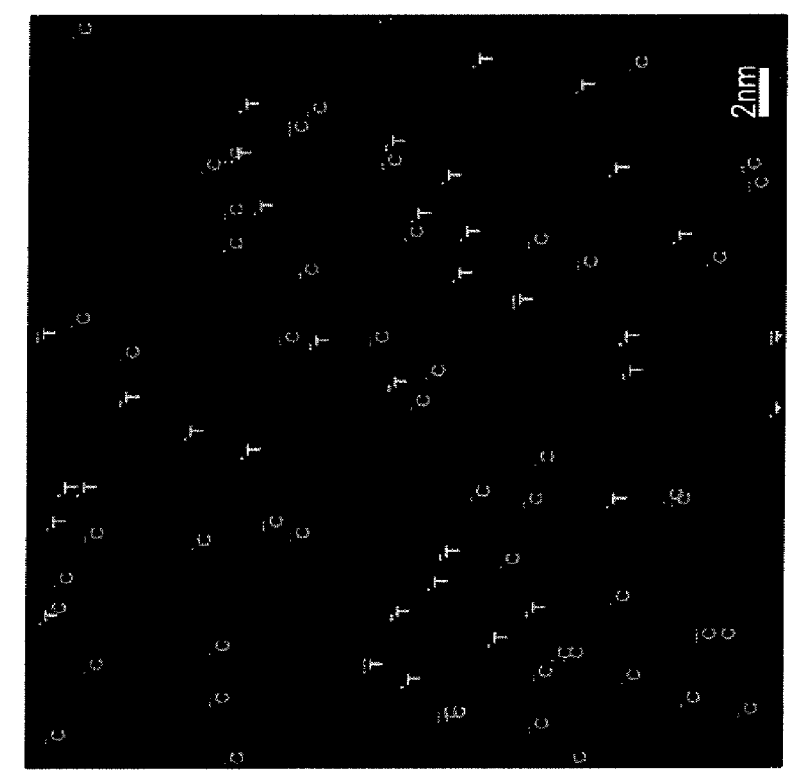
FIG. 6D
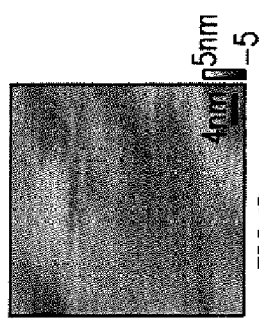
FIG. 6A
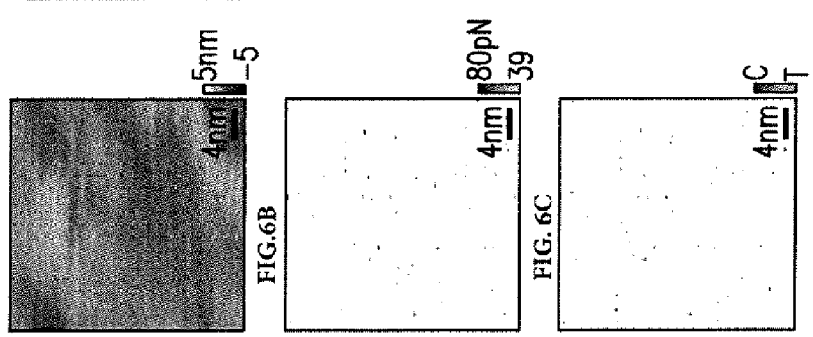
FIG. 6B
FIG. 6C

SEQUENCE LISTING

<160> NUMBER OF SEQ ID NOS: 15

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic probe

<400> SEQUENCE: 1
acctgacccg ggttt     15

<210> SEQ ID NO 2
<211> LENGTH: 9
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2 cccgggttt                                                                 9

<210> SEQ ID NO 3
<211> LENGTH: 6
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3 gggttt                                                                    6

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4 tttttteccc cc                                                            12

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
aaaaaagggg gg                                                            12

<210> SEQ ID NO 6
<211> LENGTH: 12
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
aaaaaagggg gg                                                            12

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
aaacccgggt caggt                                                         15

```
<210> SEQ ID NO 8
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8 aaacccggg                                                                 9

<210> SEQ ID NO 9
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9 aaaccc                                                                    6

<210> SEQ ID NO 10
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10 aaaaaa                                                                    6

<210> SEQ ID NO 11
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 gggggg                                                                    6

<210> SEQ ID NO 12
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12 tttttt                                                                    6

<210> SEQ ID NO 13
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 cccccc                                                                    6
```

```
<210> SEQ ID NO 14
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14 tttttt                                                              6

<210> SEQ ID NO 15
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15 cccccc                                                              6
```

DEVICES AND METHODS FOR DETERMINING MOLECULAR STRUCTURE

CROSS-REFERENCE TO RELATED APPLICATIONS

This application is a continuation of PCT Application No. PCT/US2014/061230, filed on Oct. 17, 2014, which claims priority to U.S. Provisional Application Ser. No. 61/892,274, filed on Oct. 17, 2013, each of which are incorporated by reference herein and from which priority is claimed.

SEQUENCE LISTING

The specification further incorporates by reference the Sequence Listing submitted herewith via EFS on Apr. 15, 2016. Pursuant to 37 C.F.R. § 1.52(e)(5), the Sequence Listing text file, identified as 070050.5696_SL, is 3,813 bytes and was created Apr. 15, 2016. The Sequence Listing, electronically filed herewith, does not extend beyond the scope of the specification and thus does not contain new matter.

BACKGROUND

The disclosed subject matter relates to devices and methods for determining molecular structure. Atomic force microscopy provides for imaging utilizing measurements of force between a probe and the surface of an object to be imaged. When the stylus is brought into contact with the surface, it can become deflected by forces in accordance with Hooke's Law. This deflection can be measured and recorded, such that the atomic force microscope can produce a 3-D surface map of the object under inspection.

Scanning probe microscopes (SPMs), for example, atomic force microscopes, can allow imaging and chemical characterization of surface down to the atomic scale. The localized tip-sample interactions in SPMs limit high resolution images to the topmost atomic layer of surface. Consequently, characterizing the 3-D inner structure of materials and biomolecules can be difficult for SPMs.

Scanning probe microscopes (SPM) can be operated in so-called tapping mode, where the probe or stylus comes into intermittent contact with the surface to be imaged. Operation in tapping mode can avoid causing damage and prevent the probe from sticking to the surface, while ensuring that the probe is close enough to the surface to produce high quality images. The probe can be capable of not only physically imaging the sample but identifying its biochemical composition.

However, using a probe to obtain information about the chemical identities of atoms and molecules on the Angstrom scale can necessitate imaging modalities that operate under vacuum, which can be ill-suited for biomolecules in a solution. Accordingly, there exists a need for an improved imaging technique for determining molecular structure.

SUMMARY

The disclosed subject matter provides devices and methods for determining the structure of a molecule. In an exemplary embodiment, a method of determining the structure of a molecule can include labeling a first location on the molecule with a first DNA strand. The method can include measuring a force-time waveform using the twisting of a T-shaped atomic force microscope cantilever scanning across the molecule. The cantilever can include a DNA probe having a first region that is complimentary with the first DNA strand.

In some embodiments, the molecule can be a protein. In some embodiments the molecule can be one of a protein complexed with DNA, a protein complexed with RNA, a protein complexed with both DNA and RNA, a sugar or a lipid. Labeling a first location can include replacing a native amino acid located at the first location with a first replacement amino acid and binding the first DNA strand to the first replacement amino acid. Labeling the first location can also include binding a biotin molecule to the first location, and binding the biotin molecule to the first DNA strand.

In some embodiments the method can include labeling a second location on the molecule with a second DNA strand. The DNA probe can include a second region that is complimentary with the second DNA strand. Labeling the second location can include replacing a native amino acid located at the second location with a second replacement amino acid and binding the second DNA strand to the second replacement amino acid. Labeling the second location can include binding a biotin molecule to the second location, e.g., the biotin molecule can be bound to the second DNA strand.

In some embodiments, the method can include labeling a plurality of locations on the molecule with a plurality of DNA strands. The DNA probe can have a complimentary region for each of the DNA strands. The method can include measuring pairwise distances between each of the DNA strands. In some embodiments, the method can include determining a three-dimensional structure based at least in part on the pairwise distances.

In some embodiments, the first DNA strand can be between 2 and 30 base-long single-stranded DNA. Scanning can include a fluid tapping mode.

According to another exemplary embodiment, an atomic force microscope for determining the structure of a molecule having a first location labeled with a first DNA strand is provided. In one arrangement, the atomic force microscope can include a cantilever. The cantilever can have a body having a T-shaped geometry including a base, a first end and a second end. The cantilever can include a tip, disposed at one of the first and second end. The cantilever can include a DNA probe. The DNA probe can be coupled to the tip, and have a first region that is complimentary to the first DNA strand.

In some embodiments, the body can be silicon nitride. The tip can be silicon. The cantilever can have a resonance frequency between 4 and 1.2 MHz. The cantilever can have a spring constant of the vertical deflections between 35 pN/nm and 200 pN/nm. The cantilever can have a spring constant of torsional modes between 200 pN/nm and 400 pN/nm. In some embodiments the DNA probe can include a second region that is complimentary to a second DNA strand coupled to a second location on the molecule.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE FIGURES

FIG. 3A-FIG. 3F illustrate chemically-specific imaging and 3D reconstruction using DNA labels.

FIG. 6A-FIG. 6F illustrate imaging of DNA molecules immobilized directly onto a substrate.

DETAILED DESCRIPTION

Devices and methods for determining the structure of a molecule are disclosed herein. For example, the presently disclosed subject matter can provide techniques to determine chemical identities with Angstrom scale spatial resolution though the use of a specially equipped atomic force microscope (AFM).

Figure 1:
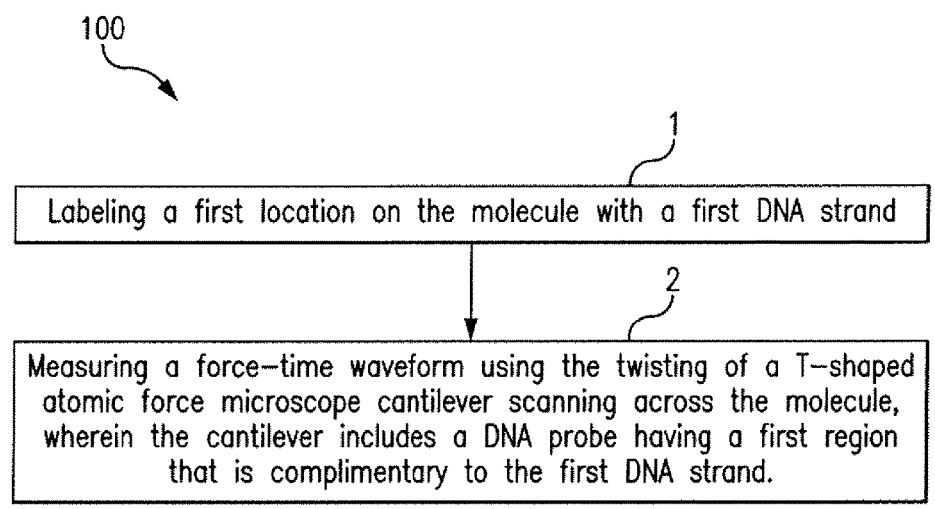
FIG. 1 shows an exemplary method for determining the structure of a molecule in accordance with the disclosed subject matter.

According to one aspect of the disclosed subject matter, a method determining the structure of a molecule is provided. The method can include chemo-mechanical labeling employing single-stranded DNA to label target sites on a biomolecule. A nanomechanical readout mechanism based on atomic force microscopy can be used to locate the chemo-mechanical labels. The chemo-mechanical labeling method can generate multi-color images wherein the sequence of DNA encodes color information. The disclosed subject matter can be utilized for chemically-selective imaging to investigate single biomolecules with sub-molecular chemical and structural detail. FIG. 1 shows, for the purpose of illustration and not limitation, a method 100 for determining the structure of a molecule in accordance with the disclosed subject matter. The molecule can be a biomolecule, for example, a protein, proteins in complex with RNA and/or DNA, or proteins in complex with other proteins, lipids, or sugars. The method can include labeling a first location on the molecule with a first DNA strand (1). In some embodiments, the method can include labeling a second location on the molecule with a second DNA strand. In some embodiments, labeling the first and/or second locations can include replacing a native amino acid with a first and second, respectively, replacement amino acid bound to the first and second, respectively, DNA strand. In some examples, a biotin molecule can be used as a replacement amino acid at the first or second location. In some embodiments, replacement amino acids can include cysteine, lysine, and tyrosine. These amino acids can bind to DNA that is modified specifically to these amino acids. The replacement amino acids can be bound to the first or second DNA strand, and the DNA strand can be used to label the first or second location, respectively. For example, the disclosed subject matter can be utilized to image the location of biotins bound to a single streptavidin molecule. The first DNA strand and the second DNA strand can be 6-base-long single stranded DNAs. The DNA strand can range between a 1-base-long strand to a 30-base-long strand. In some embodiments, the strands can be 15- or 9-base long single stranded DNAs. In some embodiments the number of bases can be selected based on the resonance frequency of the cantilever.

The method can include measuring a force-time waveform using the twisting of a T-shaped atomic force microscope cantilever scanning across the molecule (2). It some embodiments the method can use any known technique for using an atomic force microscope to measure force-time waveforms. The cantilever can include a DNA probe having a first region that is complimentary with the first DNA strand. In some embodiments, the probe can have a second region that is complimentary with the second DNA strand.

In some embodiments, scanning can include a fluid tapping mode. Fluid tapping mode includes vibrating the cantilever and adjusting the relative position of the cantilever to the surface under feedback control so that the vibration amplitude remains constant. Alternatively, the feedback can include measurement of the peak tapping force and keeping it constant.

Figure 2:
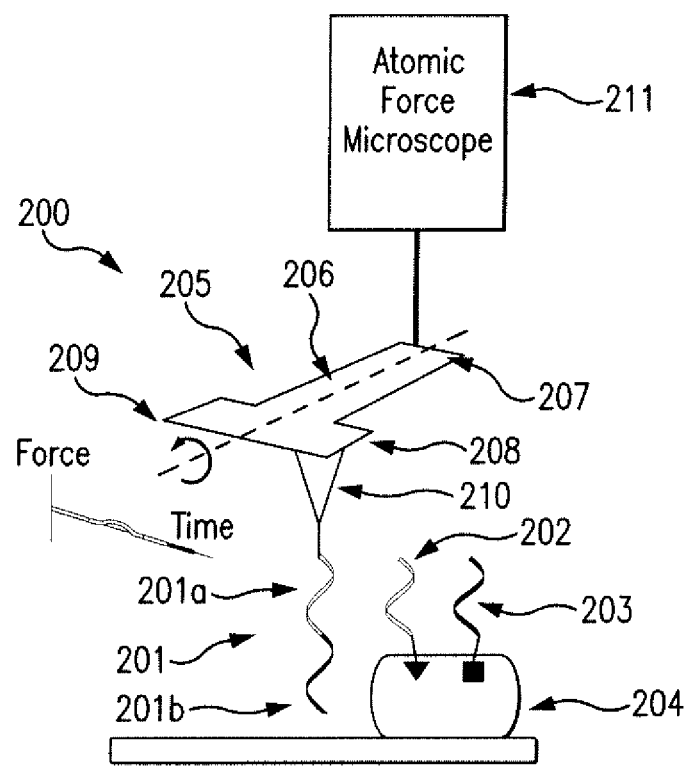
FIG. 2 illustrates an atomic force microscope including a cantilever in accordance with the disclosed subject matter.

In an exemplary embodiment of the disclosed subject matter, an AFM for determining the structure of a molecule having first and second locations labeled with first and second DNA strands is provided. Referring to FIG. 2, for the purpose of illustration and not limitation, the device 200 can include an atomic force microscope 211 (illustrated as a box) which can include a cantilever 205. The atomic force microscope can utilize cantilevers 205 with a custom geometry, including a body and a wider region at the free end. For example, the cantilever can have a body 206 having a T-shaped geometry. The T-shaped geometry can include a base 207, a first end 208, and a second end 209. The first 208 and second 209 ends can have a width of about 100 µm, and can be, for example about 60 µm. In some embodiments the first 208 and second 209 ends can have a width of 10 µm. The body 206 can be silicon nitride. The body 206 can be other materials, for example silicon.

The cantilever 205 can also include a tip 210. The tip 210 can be disposed on one of the first end 208 and second end 209. The tip 210 can be silicon.

The device 200 can include a DNA probe 201 coupled to the tip 210. The DNA probe 201 can include a first region 201a. The first region 201a can be complimentary with a first DNA strand 202 coupled to a first location on molecule 204. In some embodiments, the DNA probe 201 can include a second region 201b. The second region 201b can be complimentary with a second DNA strand 203 coupled to a second location on molecule 204. In some embodiments the DNA probe can have additional regions that can be complimentary to additional DNA strands coupled to molecule 204.

In some embodiments, the cantilever can have a resonance frequency between 4 and 1.2 MHZ. The cantilever can have a spring constant of the vertical deflections between 35 pN/nm and 200 pN/nm. The cantilever can have a spring constant of torsional modes between 200 pN/nm and 400 pN/nm.

Figure 4A:
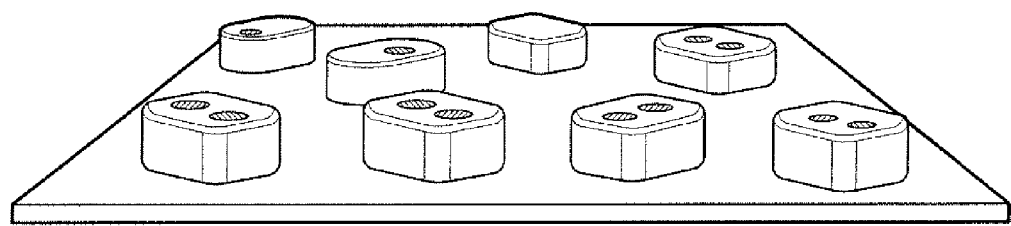
FIG. 4A and FIG. 4B illustrate locating specific chemical targets with high spatial-resolution and reconstructing the 3-D locations of targets from their pairwise distances.
Figure 4B:
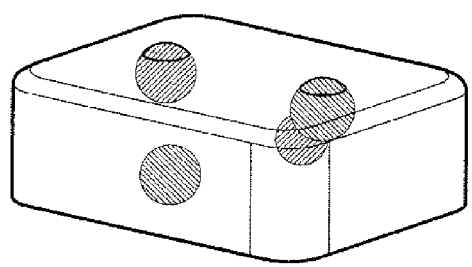

According to another aspect of the disclosed subject matter, an atomic force microscope can operate by measuring forces between biomolecules and how these forces change over time or distance. The disclosed subject matter provides for the conversion of chemical information into a time or distance signal, which can be measured by the atomic force microscope. The disclosed subject matter also provides techniques for encoding and decoding information in energy landscapes of single biomolecular interactions. This can be accomplished by designing DNA molecules that can hybridize to multiple targets, each creating a distinct force-extension curve and having a lifetime tuned to the resonance frequency of an atomic force microscope cantilever. The disclosed subject matter also provides techniques for generating multicolor images of distinct DNA molecules with a resolution greater than 1 nm. Referring to FIG. 3, for the purpose of illustration and not limitation, FIGS. 3A-3C illustrate chemically-specific imaging and 3-D reconstruction using DNA labels. A strand of DNA, the probe 201, can interact with target DNA strands having shorter sequences 202, 203. The DNA strands 202, 203, can be coupled to a molecule 204 at known locations. Sequences of the target DNA strands can be complementary to different regions along the probe DNA 201. For example, region 201a can be complementary with DNA strand 202 and region 201b can be complementary with DNA strand 203. Formations of duplexes can create distance force-time waveforms, which can be detected by the twisting of T-shaped AFM cantilevers 205. For example, the pulling forces exerted by the target molecules can appear as negative peaks in the force-time waveforms. FIGS. 3D-3F show examples of experimentally measured waveforms corresponding to FIGS. 3A-3C, respectively. Mapping the timing of pulling events across the sample surface can allow locating specific chemical targets with high spatial resolution (for example as illustrated in FIG. 4A) and/or reconstructing the 3-D locations of targets from their pairwise distances (for example as illustrated in FIG. 4B).

Example 1

In accordance with the disclosed subject matter, imaging and three-dimensional reconstruction of chemical groups inside a protein complex using atomic force microscopy is demonstrated. Short single-stranded DNAs can be employed as imaging labels linked to target regions inside a protein complex. T-shaped AFM cantilevers functionalized with complementary probe DNAs can allow locating the labels with sequence specificity and sub-nanometer resolution. After measuring pairwise distances between labels, the 3D structure formed by the target chemical groups within the protein complex can be reconstructed using geometric calculations. Examples with biotin-streptavidin complex showed that the predicted 3-D loci of the carboxylic acid groups of biotins were within 2-Angstroms of their respective loci in the corresponding crystal structure. Therefore, scanning probe microscopes can complement certain structure biological techniques in solving structures that are difficult to study due to their size and complexity.

The temporal characteristics of dynamic tip-sample interactions can be utilized to image material properties with high spatial resolution. The ability to probe interaction forces with good time resolution can also lead to detecting short-lived biomolecular interactions and harnessing them for chemically specific imaging purposes. For example, short-single-stranded DNA molecules can be used as labels attached to target chemical groups within biomolecules to allow chemically specific imaging and 3-D reconstruction.

Referring again to FIGS. 3 and 4, FIG. 3 illustrates how sequence dependent binding geometries of DNA can allow detecting and discriminating DNA sequences from the temporal characteristics of the forces measured by the AFM 200. The molecular configuration of the probe 201 and targets facilitate the rupture of the orange duplex to be delayed because the single-stranded green region 202 has to be stretched first. This labelling strategy can be used to image chemical groups within biomolecular complexes and reconstruct their 3-D locations (FIGS. 4A, 4B).

Partial hybridization of DNA can create complications. Any unpaired base can increase the length of the region that requires stretching, which can make it difficult to rely on rupture times to discriminate DNA sequences. (As used herein, rupture time is defined relative to the beginning of cantilever oscillation period, which is when the tip is at its highest position.)

Figure 5B:
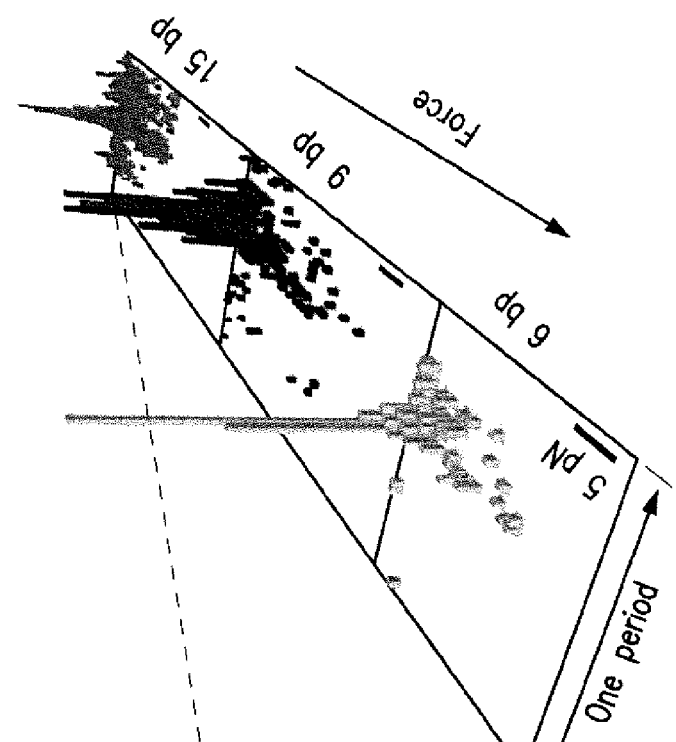
FIG. 5A-FIG. 5E illustrate tuning the lifetime of DNA interaction enhances target specificity
Figure 5A:
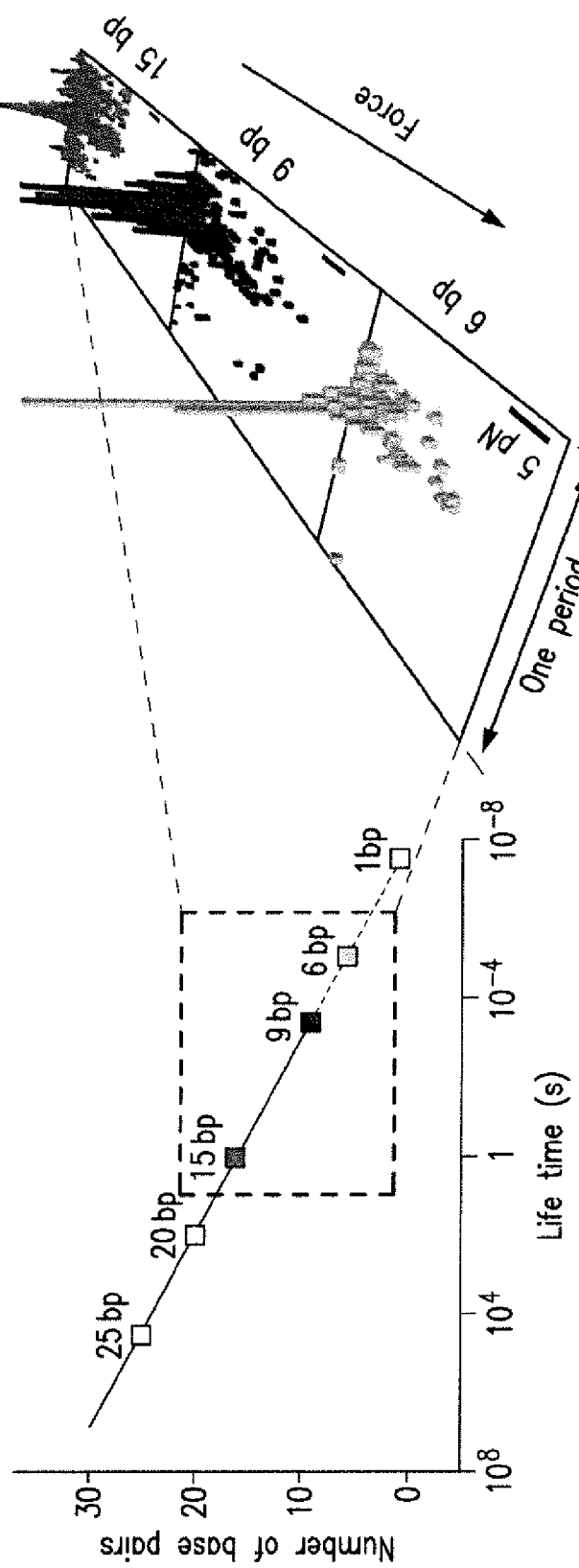

The role of partial hybridizations can be minimized by taking advantage of their reduced lifetimes relative to fully hybridized DNAs. FIG. 5A depicts, for the purpose of illustration and not limitation, an approximate trend of duplex DNA lifetimes. If the lifetime of the partially hybridized DNA were longer than the experiment duration, the measurements would incorporate events that belong to partial hybridizations. However, by choosing a sufficiently short length of DNA, the lifetime of partially hybridized interactions can be kept below the experiment duration, which can minimize the spread of detected rupture times. FIG. 5B illustrates a reduction in the spread of rupture times for 15-, 9-, and 6-base long DNA.

Referring again to FIG. 3, the probe 201 can be a 12-base probe DNA, and target strands 202, 203 can be 6-base complementary target DNAs. For example, one can have a sequence $A_6$ and the other can have the sequence $G_6$. In some embodiments, any sequence can be used, as long as there is a complimentary region on the probe 201.

In a first embodiment, targets can be directly attached to a substrate and not to other biomolecules. Rupture times measured on a $A_6$-only surface (FIG. 5C) and on a $G_6$-only surface (FIG. 5D) show that the measured distributions are located in temporally distinct regions of the oscillation period. Furthermore, on a surface with both $A_6$ and $G_6$, the distribution of rupture times reproduced a superposition of the original peaks (FIG. 5E). These observations demonstrate the ability to rely on rupture times to discriminate short target DNAs.

In an exemplary embodiment, rupture forces (FIG. 6B) and rupture times (FIG. 6C) can be recorded across a sample of DNA targets immobilized directly onto a substrate, this time with sequences $C_6$ and $T_6$. Locations where rupture forces exceeded the noise threshold value of 39 pN were identified and then corresponding rupture times were examined to determine whether the observed events belong to the targets. FIG. 6D illustrates the resulting multicolor image, which exhibits rupture events that are separated from their nearest neighbors by 0.2 nm to 10 nm. Several pixels appear as clusters. The clusters can allow estimating the resolution limit and localization accuracy of the imaging system.

FIG. 6E illustrates a plot of the distribution of distances from nearest neighbors. The histogram shows that nearly half of the detected events are within less than 1 nm distance. The remaining events exhibit a distribution that closely matches the probability distribution function p(x) corresponding to randomly located particles, $p(x)=2\pi\lambda x e^{-\pi\lambda x^2}$ where λ corresponds to particle density and x corresponds to particle spacing. The observation can suggest that clustering is not random and comes from repeated measurements of the same target. (The possibility of multiple probes interacting with targets can be ruled out. For this to explain clustering, probes have to be less than 1 nm apart.)

Statistical analysis of clusters can provide calculable information about the resolution limit and the accuracy of the color assignments. Because clusters originate from repeated rupture events of the same target DNA, the special extents observed in the ensemble of clusters (FIG. 6F) represent the point spread function (PSF) of the imaging system whose full width at half maximum (FWHM) corresponds to the resolution limit. The PSF can be approximated with a Gaussian profile and the variances ($\sigma^2$) calculated for each cluster can be averaged to estimate the root-mean-square size of the PSF ($\sigma$), which can be related to the limit of resolution (FWHM~2.4σ). Along the horizontal and vertical directions, resolution limits can be estimated as 0.47 nm (σ=0.20 nm) and 0.58 nm (σ=0.24 nm), respectively. In addition, the localized accuracy (given with $\sigma/N^{1/2}$), where N is the number of rupture events in a cluster) is better than 0.25 nm (note that the positioning accuracy of the piezoelectric scanner is not included in this estimate). The extremely small limit of resolution is attributed to small sizes of the probe and target molecules. The contour length of a 6-base long DNA strand (~3.8 nm) is comparable to its persistence length (2 to 3 nm), which can limit the reach of the probes and targets.

The color uniformity of clusters can allow estimating the accuracy of color assignments. About 88% of the 299 clusters were completely $T_6$ or $C_6$ and only ~4.3% had equal number of $T_6$ and $C_6$. The strong correlation between color assignments within a cluster can suggest that interactions between the probe and target DNAs are detected with sequence specificity. Varying the tip and sample combinations can verify the repeatability of color uniformities seen in clusters, as well as the resolution limits estimated from the physical sizes of clusters.

The clusters in FIG. 6F are predominantly horizontal. A reason can be the raster scan pattern of the AFM. While the scanning tip moves continuously in the horizontal direction, it can make discrete steps in the vertical direction. If considering two cases where a target molecule is located halfway between the centers of pixels in the horizontal and vertical directions, the one in the horizontal direction is more likely to be detected because the tip will gradually move over it. Furthermore, this target is likely to be detected as a cluster by appearing in the two adjacent horizontal pixels. In the case of the target located halfway between pixels in the vertical direction, the tip will skip the target as it moves from one scan line to the next. This can lower the probability of the target being detected in the adjacent vertical pixels.

Figure 7B:
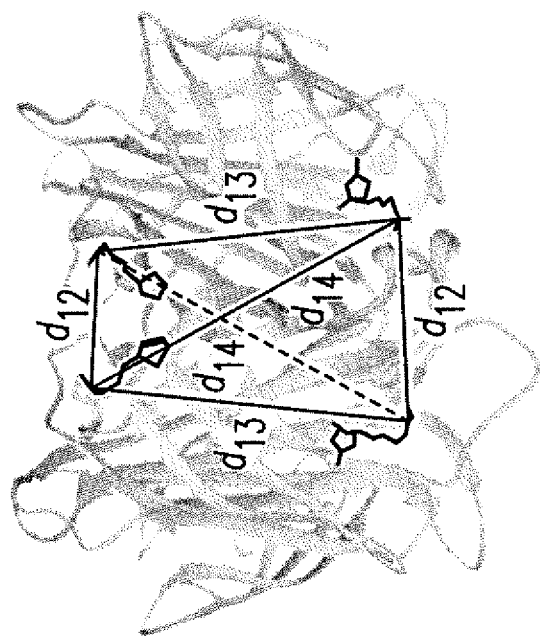
FIG. 7A-FIG. 7E illustrate chemically specific imaging and 3-D reconstruction in a protein complex.
Figure 7A:
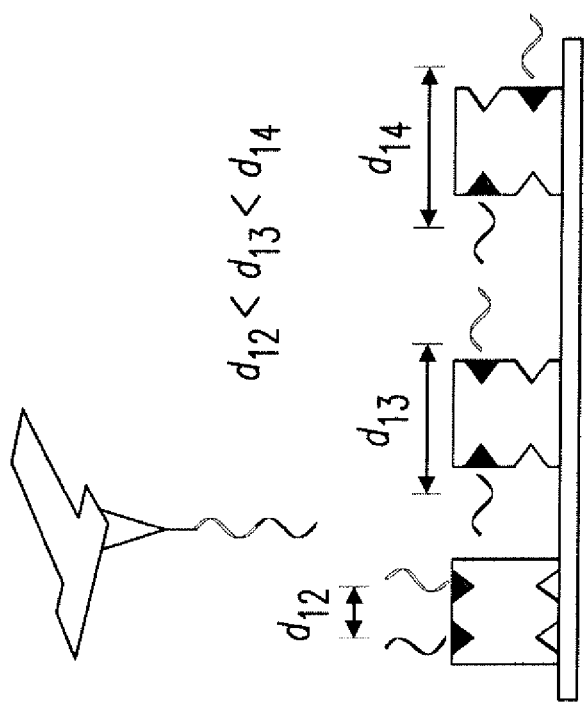

In an exemplary embodiment, devices and methods of the disclosed subject matter were used to locate chemical groups within single biomolecules by attaching 6-base-long single-stranded DNAs to target chemical groups. Biotin-streptavidin complexes were used. Streptavidin has four binding sites for biotin. Due to the symmetry of the crystal structure, the distances between pairs of carboxylic acids (the sites where DNA labels are linked to biotins) can have three distinct values (FIGS. 7A, 7B). As a result, carboxylic acids of biotins form a tetrahedron with opposite edges having equal length.

Figure 7D:
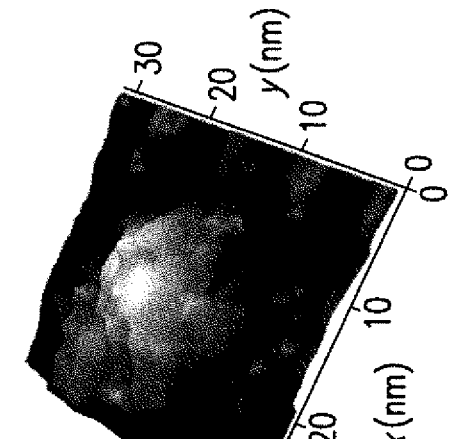
Figure 7C:
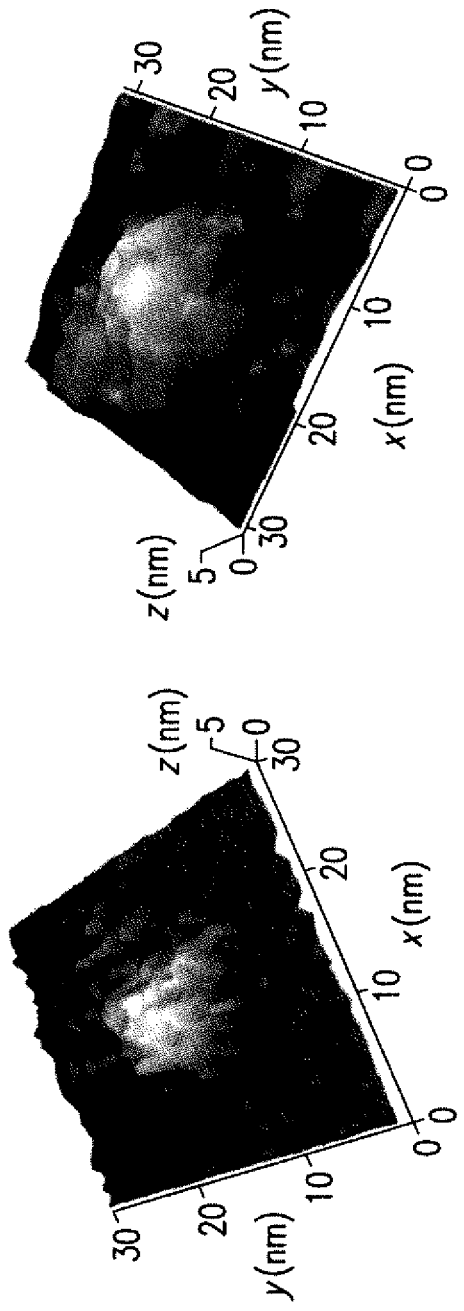

FIGS. 7C and 7D show grayscale height images of streptavidin complexed with DNA-labelled biotins, with the locations of detected rupture events highlighted with color. A set of 12 additional images are given in FIG. 7E. Similar to the results in FIG. 6D, clustering of rupture events was observed. The clusters are predominantly composed of single colors, suggesting that color assignments are accurate even when targets are bound to proteins. Although one DNA sequence is sufficient to label biotins, two sequences were used to test if sequences can be discriminated reliably when targets are bound to proteins, which can help with studies of more complex systems.

Figure 7E:
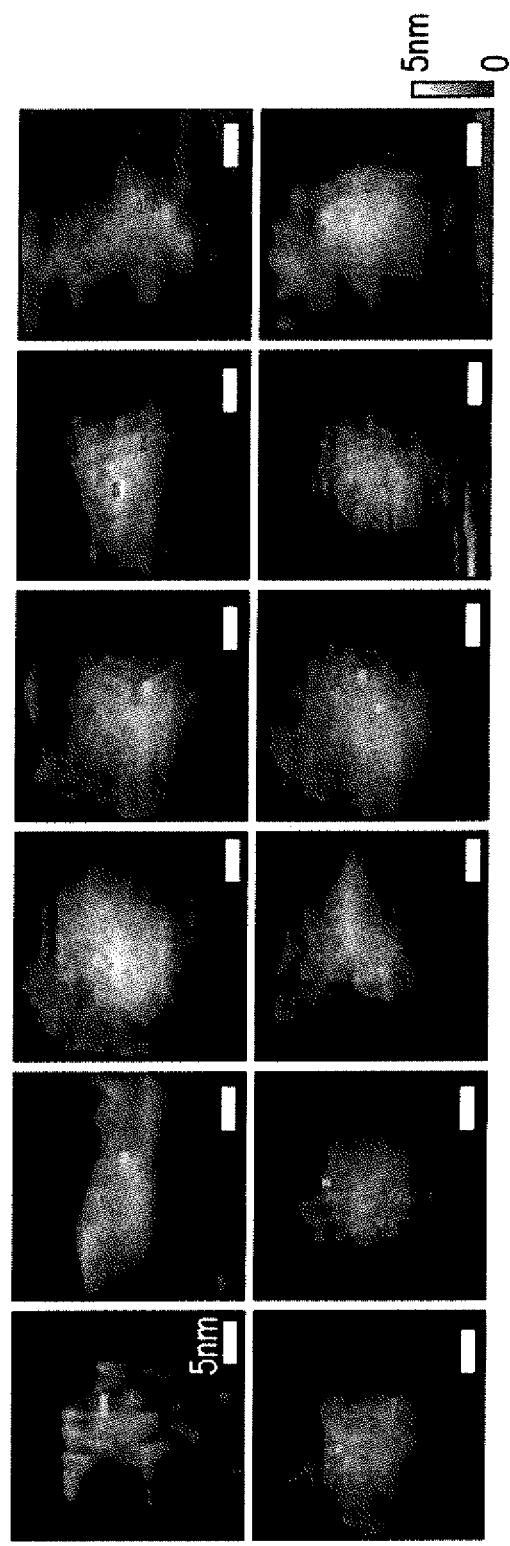

The images in FIG. 7C-E typically show two distinct locations for rupture events despite the four binding sites of streptavidin. This is because only those label DNAs that are oriented towards the tip are likely to bind. Label DNAs that are oriented towards the substrate have to bend in order to hybridize with the probe DNA, which can reduce their binding probability.

Figure 8A:
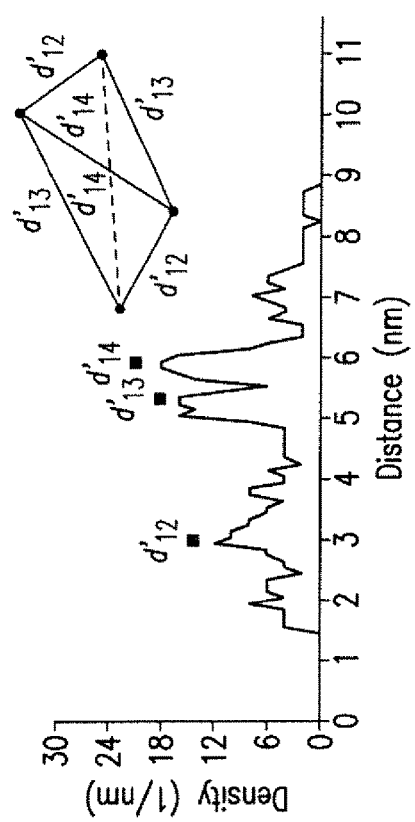
FIG. 8A-FIG. 8C illustrate data related to the relative positions of probe and target DNAs.

The distance values between the pairs of rupture locations seen in each image exhibit clustering around two values: 5.3 nm and 6.0 nm (FIG. 8A). A less prominent clustering is seen around 3.0 nm. Proceeding with the assumption that these three values reflect the distances between the midpoints of label DNAs, (this would be the approximate configuration that requires the least amount of bending energy, as illustrated in FIG. 8C), shape of the tetrahedron whose corners correspond to the midpoints of DNA was determined by solving algebraic equations satisfied by the coordinates of the corners. The locations of carboxylic acids were estimated by translating the corners of the tetrahedron towards its center of mass by a distance equal to 11 Angstroms (approximate length of 3 base long duplex DNA). The new coordinates represent the predicted 3-D locations of the carboxylic acids relative to each other. These geometrical calculations involve a number of assumptions.

First, the label-DNAs would orient approximately normal to the surface of the protein due to electrostatic repulsion and that surface normal can be approximated with the radial line pointing away from the center of mass. Any errors due to deviations from this approximation can be small because of the short length of the 3-base long duplex DNA. Additionally, it was assumed that the 6-carbon aliphatic linker that connects DNA to carboxylic acid would orient approximately in the direction of the carbons C1 and C3 of the biotin (C1 belongs to the carboxylic acid. C2 was skipped to account for bond angles in the carbon chain). This direction is approximately orthogonal to the radial line from the center of mass, hence does not contribute to the radial position of labels in a significant way. Furthermore, deformations of the molecular complex under the applied force were neglected because the peak tapping forces were limited to 10 pN.

Figure 8B:
Figure 8C:
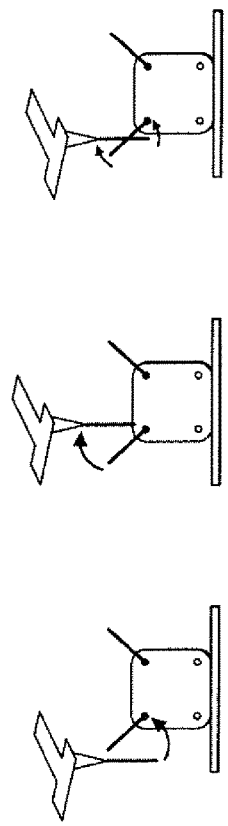

FIG. 8B shows a comparison of the predicted locations of carboxylic acids, represented with yellow spheres, with the crystal structure of the biotin-streptavidin complex. The carboxylic acids in the crystal structure are located at the Y-shaped ends of the red colored biotins. To make this comparison the center of masses of the predicted 3-D geometry and the crystal structure were aligned, and then two of the carboxylic acids in the crystal structure (carbon in the carboxylic acid of the biotins) were used as reference points to orient the predicted geometry such that the distance between the two references and their two counterparts in the predicted geometry are minimized. As seen in FIG. 8B, despite the approximations, there is a good degree of agreement, within 2 Angstroms, between the predicted locations with their counterparts in the crystal structure. This demonstrated capability of determining 3-D locations of chemical groups in biological macromolecules underscores the need for scanning probe microscopes in structural biology where large biomolecular complexes can pose challenges to certain technologies.

In certain embodiments of the disclosed subject matter, cantilevers with a custom T-shaped geometry can be used, and are commercially available from, for example, Applied Nanostructures, Inc. Santa Clara, Calif. and Bruker-Nano, Santa Barbara, Calif. The body of cantilevers can be made of silicon nitride and the tip can be made of silicon. The resonance frequencies of the cantilevers in solution can be between 4 and 1.2 MHz as determined from thermal noise spectrum. The spring constant of the vertical deflections range can be from 35 pN/nm to 200 pN/nm, each calibrated against the thermo-mechanical noise.

The spring constants of the torsional modes (200 pN/nm-400 pN/nm) can be calibrated against the thermal noise spectrum of torsional deflections. This calculation requires the knowledge of tip offset distances, which can be determined using scanning electron microscopy. There can be variations in resonance frequencies and spring constants, because cantilevers with different lengths can be used. Longer cantilevers can provide a better time resolution due to higher ratio of torsional to flexural resonance frequencies (~13.5) compared to the shorter cantilevers (~7). Cantilevers can have a length between 300 µm and 10 µm. The shorter cantilevers can provide improved signal to noise ratio, but they underestimate the magnitude of rupture forces due to filtering.

The tips can be cleaned by immersing cantilevers into an acidic solution (nitric acid/H2O, 1:2) for 20 min. After rinsing with de-ionized water, the tips can be dried overnight under nitrogen atmosphere. To generate amino-groups, the cleaned tips can be placed in an anhydrous toluene solution containing 1% APDES (e.g., 3-aminopropyl diethoxymethyl silane, commercially available from, for example, from Gelest) for 3 hours and under nitrogen atmosphere. After the reaction, the tips can be rinsed with toluene gently and then baked at 95° C. for 30 min. Then the tips can be washed with toluene, methanol, and de-ionized water sequentially. The resulting amino-functionalized tips can be dried in a chamber under nitrogen atmosphere.

Next, heterofunctional crosslinkers such as SM (PEG)$_2$ (N-hydroxysuccinimidyl-(ethylene glycol)2-maleimide), commercially available from, for example, Thermo Scientific, which contains maleimide and N-hydroxysuccinimide (NETS) groups at its ends via two ethylene glycol repeats, can be allowed to the tips to generate maleimide-functionalized surface. The tips can be placed in a crosslinker solution (1 mg in 100 µL of phosphate buffered saline (PBS) (pH 7.4)) and incubated for 90 min. After the reaction, the tips can be rinsed with a PBS buffer, e.g., dimethyl sulfoxide (DMSO), for example, methoxy sulfide, commercially available from, for example, Sigma Aldrich, de-ionized water sequentially. Finally, DNA molecules can be immobilized on the surface by placing the tips in a thiolated oligonucleotide solution, commercially available from, for example, Integrated DNA Technologies, Inc., as a 10 µM in PBS, overnight. After the incubation, the tips can be washed with PBS and de-ionized water.

Note that the tip functionalization method does not ensure that there will be a single DNA probe at the tip. However, due to the small sizes of probes and targets, probes that are further away from the very end of tip can have a lower probability of binding. There can be an energy barrier imposed by the stretching of the probe, which will reduce binding probability.

A silicon wafer can be used as a substrate. The identical cleaning and modification procedures as tip functionalization can be applied. To create samples with mixed target sequences, the final concentration of each DNA sequence can be adjusted to 5 µM or 10 µM (FIG. 3*d*). After preparation, the substrate can be mounted on an AFM sample stage for imaging. Imaging can be performed in PBS (pH 7.4).

DNA-bound biotin-streptavidin sample preparation will next be described. A stock solution of streptavidin (available from Sigma Aldrich) in 1 mg ml-1 PBS (pH 6.8) can be made and can be diluted with PBS (pH 6.8) to a final concentration of 0.1 mg mL-1 for each experiment. A 60 uL of the diluted solution can be dropped onto a freshly cleaved mica surface (available from VWR). After 1 hour, the mica surface can be washed with PBS (pH 6.8) and subsequently incubated overnight in a solution containing DNA targets modified with a biotin at its 5' end (source: Integrated DNA technologies, Inc., 10 µM for each target in PBS (pH 6.8)). After the incubation, the surface can be washed with PBS (pH 6.8) and mounted on the AFM sample stage for imaging. Imaging can be performed in PBS (pH 6.8).

AFM testing with two commercial AFM systems, BioScope II and Multimode V, Bruker-Nano, Inc., were performed. Imaging can be carried out in fluid tapping mode at room temperature (20° C.). Torsional deflection signals from T-shaped cantilevers can be analyzed in real time to create rupture force and rupture time maps. Rupture force is defined as the minimum value (most negative) of the tip-sample force waveform. Rupture time is defined as the temporal location of the minimum force value within a single oscillation period. The highest point of the tip determines the beginning and the ending of the period. The analysis can be carried out in Labview (available from National Instruments) with a computer equipped with a data acquisition card, such as the NI-56115. The NI-56115 card can have a sampling rate of 10 MHz. In some embodiments, other sampling cards with a sampling rate above 400 KHz can be used.

Algorithms can be used to calculate tip-sample force waveforms. During the imaging the drive amplitudes can be adjusted to maintain peak tapping forces to be below 10 pN, which can be expected to minimize the deformations of the protein surface. The set-point amplitudes can be selected according to the length of DNA molecules. For the experiments in FIG. 5, to account for differences in contour lengths of 6-, 9-, and 15-base long DNA, the peak-to-peak oscillation amplitudes can be adjusted in proportion to the number of bases and approximately equal to twice the contour length of hybridized DNA. A 0.63 nm/base can be used to approximate the contour length. For multicolor imaging, the set-amplitude value can be maintained at approximately 4 nm. The immobilized DNA surface can be imaged with a scan speed of 400 nm/sec. In the case of imaging streptavidin molecules complexed with biotinylated DNA, scan speeds around 600 to 1000 nm/sec can be used.

To identify the locations of rupture events, a threshold force level beyond which a measured pulling force is considered as a rupture event between the complementary probe and target. For this, one can compared force histograms recorded on fully complementary targets and non-complementary targets and select the value beyond which the events counted on non-complementary surface is less than 5% of the events counted on complementary DNA surface. The resulting error rate of 5% represents a compromise for minimizing false positives (selectivity) and false negatives (sensitivity).

The threshold values were 12-14 pN for FIG. 5 and 39-49 pN for FIG. 7. The limited torsional bandwidth of the shorter T-shaped cantilevers used in the experiments underestimate the rupture forces. Because binding probability of probe and targets are low, one can incorporate rupture data from trace and retrace images into a single image for experiments on immobilized DNA samples. For DNA labels bound to biotin-streptavidin complexes, one can use trace and retrace images separately. By comparing the locations of the rupture events in trace and retrace images on DNA surfaces, it was found that approximately 50% of the events overlap (within 2 nm) with a rupture event in the other image. This suggests that detecting a single label in a single image is about 50%. Therefore combining rupture data from both images can allow detecting a majority of the labels.

To determine whether a detected rupture event corresponds to one or the other target, one can looked at the rupture time. The length of the entire period was defined as 64 units (ranging from −32 to 32, with zero corresponding to the lowest point of the tip). Based on the results in FIG. 5(c-e), rupture events between −10 and 10 can be counted as the target complementary to the base region of the DNA probe and events between 18 and 32 are counted as the target that complementary to the free end of the DNA probe. Once the target is determined, a color-coded image can be generated.

With the immobilized DNA samples, one can determine clusters in rupture events and characterized the spread of the each cluster. Clusters can be defined such that a given pixel representing a rupture event belongs to a cluster if at least one of the elements of the cluster is within 0.68 nm (3.5 pixels). This threshold can be determined by a histogram, as illustrated in FIG. 6e. With this algorithm 299 clusters were identified. The variances in horizontal and vertical directions can be calculated for each cluster using sample means. For clusters with more than two elements, the computer picked two elements randomly. The resulting variance can be averaged over the entire set of clusters. If a cluster has elements only in the same row or column, its variance is not included in the calculations for the orthogonal direction. With the biotin-streptavidin complexes, the distances between the rupture locations can be analyzed. In case of clustered pixels, one can assume the rupture location is at the center of mass of the cluster. Rupture signals that fall outside of the boundaries of streptavidin can be ignored, as these can be caused by force noise or unspecific interactions. Pairwise distance data can be analyzed by calculating the density of data points as a function of distance. A moving window that is 0.5 nm wide can be used in the density calculations.

Probe and target DNA sequences are provided in Table 1.

TABLE 1

Probe and target DNA sequences

Figure 5C:
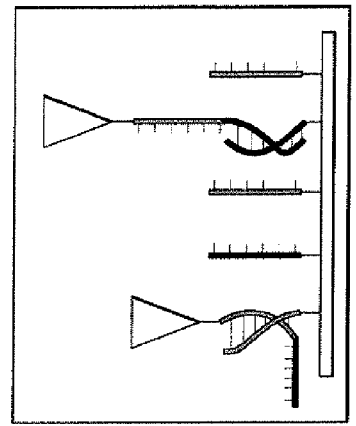
Figure 5C:
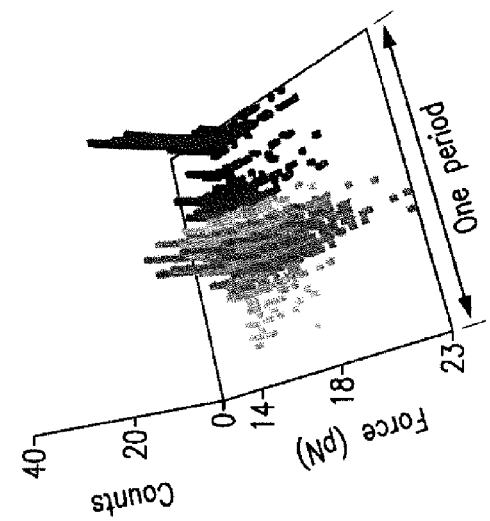
Figure 5D:
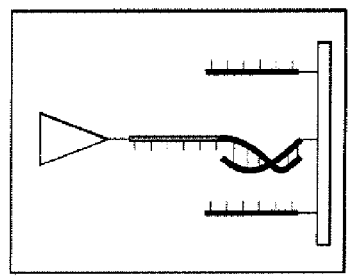
Figure 5D:
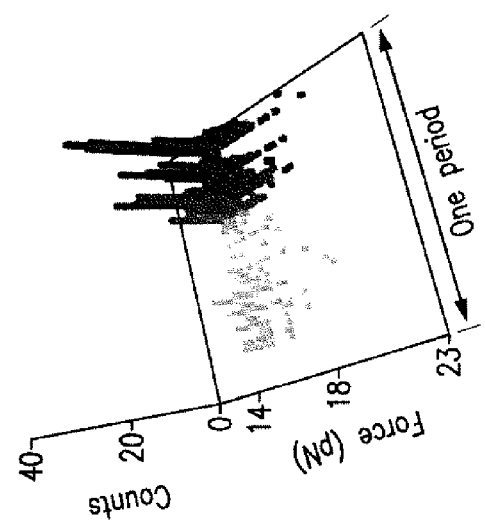
Figure 5E:
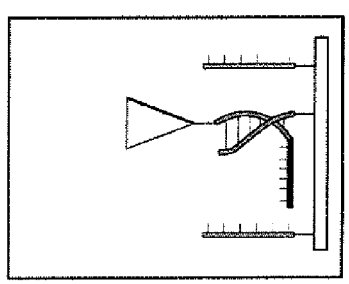
Figure 5E:
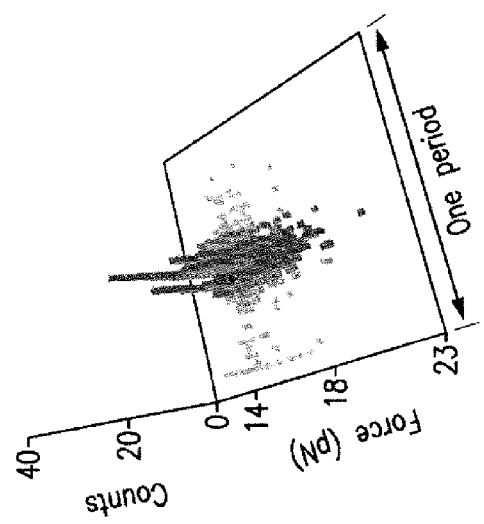

| | Probe | Target(s) |
|---|---|---|
| FIG. 5B (15-bp) | 5'-SH-ACC TGA CCC GGG TTT-3' | 5'-SH-AAA CCC GGG TCA GGT-3' |
| FIG. 5B (9-bp) | 5'-SH-CCC GGG TTT-3' | 5'-SH-AAA CCC GGG-3' |
| FIG. 5B (6-bp) | 5'-SH-GGG TTT-3' | 5'-SH-AAA CCC-3' |
| FIG. 5C-E | 5'-SH-TTT TTT CCC CCC-3' | 5'-SH-AAA AAA-3'<br>5'-SH-GGG GGG-3' |
| FIG. 6D | 5'-SH-AAA AAA GGG GGG-3' | 5'-SH-TTT TTT-3'<br>5'-SH-CCC CCC-3' |
| FIG. 7 | 5'-SH-AAA AAA GGG GGG-3' | 5'-biotin-TTT TTT-3'<br>5'-biotin-CCC CCC-3' |

While the disclosed subject matter is described herein in terms of certain exemplary embodiments, those skilled in the art will recognize that various modifications and improvements can be made to the disclosed subject matter without departing from the scope thereof. Moreover, although individual features of one embodiment of the disclosed subject matter can be discussed herein, or shown in the drawing of one of the embodiments and not in another embodiment, it should be apparent that individual features of one embodiment can be combined with one or more features of another embodiment or features from a plurality of embodiments. Thus, the foregoing description of specific embodiments of the disclosed subject matter has been presented for purposes of illustration and description. It is not intended to be exhaustive or to limit the disclosed subject matter to those embodiments disclosed.

The invention claimed is:

1. An atomic force microscope device for determining the structure of a molecule, comprising:
   a cantilever having a body with T-shaped geometry including a base, a first end and a second end;
   a tip, disposed at one of the first end and the second end; and
   a DNA probe, coupled to the tip, having a first region that is complementary to a first DNA strand coupled to a first location on the molecule;
   wherein the cantilever has a spring constant of torsional modes between 200 pN/nm and 400 pN/nm.

2. The device of claim 1, wherein the body comprises silicon nitride.

3. The device of claim 1, wherein the tip comprises silicon.

4. The device of claim 1, wherein the cantilever has a resonance frequency between 4 and 1.20 MHz.

5. The device of claim 1, wherein the cantilever has a spring constant of the vertical deflections between 35 pN/nm and 200 pN/nm.

6. The device of claim 1, wherein the DNA probe includes a second region that is complementary to a second DNA strand coupled to a second location on the molecule.

* * * * *